United States Patent [19] [11] 4,309,565
Crabbé [45] Jan. 5, 1982

[54] PROCESS FOR SYNTHESIZING A-NOR AND A-NOR-18-HOMO-STEROIDS

[75] Inventor: Pierre Crabbé, Columbia, Mo.

[73] Assignee: World Health Organization, Geneva, Switzerland

[21] Appl. No.: 140,598

[22] Filed: Apr. 15, 1980

[30] Foreign Application Priority Data

Aug. 14, 1979 [FR] France ................. 79 20926

[51] Int. Cl.$^3$ .............. C07C 69/76; C07C 67/02
[52] U.S. Cl. ........................... 560/107; 560/1; 560/257; 560/258; 568/670; 260/340.9 AS; 568/370
[58] Field of Search ........... 560/107, 1, 257, 258; 568/670

[56] References Cited

U.S. PATENT DOCUMENTS

| | | | |
|---|---|---|---|
| 3,141,025 | 7/1964 | Nominé et al. | 560/107 |
| 3,772,366 | 11/1973 | Uskokovic et al. | 560/107 |
| 3,803,218 | 4/1974 | Uskokovic et al. | 560/107 |
| 3,816,459 | 6/1974 | Uskokovic et al. | 560/107 |
| 3,932,519 | 1/1976 | Cohen et al. | 560/107 |
| 4,011,211 | 3/1977 | Cohen et al. | 560/107 |
| 4,201,869 | 5/1980 | Cohen et al. | 560/107 |

OTHER PUBLICATIONS

Sauer, G. et al., Angew. Chem. Inter. Edit vol. 14 (1975)16 pp. 417.
Wiechert, R., Angew Chem. Int. Ed. Engl 16 506–513 (1977).

*Primary Examiner*—Paul J. Killos
*Attorney, Agent, or Firm*—Cushman, Darby & Cushman

[57] ABSTRACT

The present invention is directed to a process for synthesizing A-nor and A-nor-18-homo-steroids. The invention is concerned with providing a total synthesis for the compounds called Dinordin and 18-homo-Dinordin. The preparation of other compounds will also be evident.

1 Claim, No Drawings

PROCESS FOR SYNTHESIZING A-NOR AND A-NOR-18-HOMO-STEROIDS

The present invention is related to a process for synthesizing A-nor and A-nor-18-homo-steroids. The invention is particularly concerned with providing a total synthesis for the compounds called Dinordrin and 18-homo-Dinordrin although the preparation of other related compounds will also be evident.

Dinordrin (1a) and 18-homo-Dinordrin (1b) in the form of their propionate esters, may be structurally illustrated as follows:

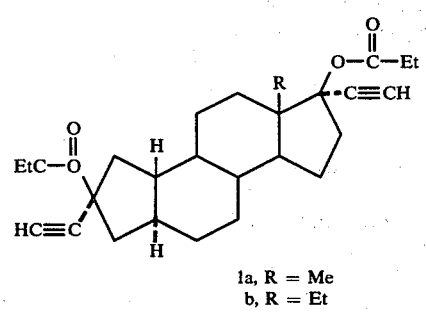

1a, R = Me
b, R = Et

These compounds have been reported to have unusual fertility inhibitor properties. For example, Dinordrin appears to be about ten times more potent than Anordrin (the dipropionate of 2α, 17α-diethynyl-A-nor-5α-androstane-2β, 17β-diol). See P. Crabbé, H. Fillion, Y. Letourneux, E. Diczfalusy, A. R. Aedo, J. W. Goldzieher, A. A. Shaikh, and V. D. Castracane, *Steroids*, 1979, 33, 85; P. Crabbé, D. Andre and H. Fillion, *Tetrahedron Letters*, 1979, 893.

Prior procedures for preparing 1a and 1b and generally similar products, including Anordrin, are inconveniently lengthy and low yielding and there is a real need for a versatile, short, total synthetic scheme for preparing these products. The principle object of the present invention is to provide such a process. A more specific object is to provide a relatively short synthetic route which affords the desired products in a convenient manner and in good yield. Other objects will also be hereinafter evident.

Broadly speaking, the products which may be prepared according to the present process include those of the Formula I:

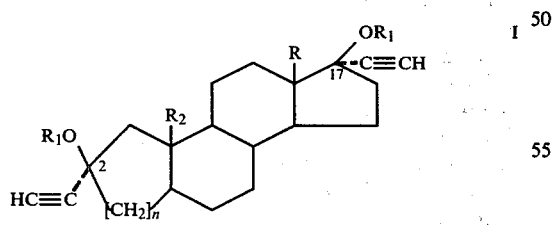

wherein n = 1 or 0, R is methyl or ethyl; $R_1$ is hydrogen or

wherein A is preferably lower alkyl, cycloalkyl or aryl; and $R_2$ is hydrogen or methyl. It will be appreciated that Dinordrin is represented by Formula I when n = 1, R is methyl, $R_1$ is a propionate and $R_2$ is hydrogen while, in 18-homo-Dinordrin, R is ethyl, $R_1$ is a propionate and $R_2$ is hydrogen.

Anordrin is represented by Formula I when n = 1, R and $R_2$ are both methyl and $R_1$ is

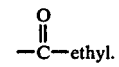

It will be appreciated that the products are normally prepared as mixtures of the 2α, 17α-ethynyl and 2β, 17α-ethynyl isomers. The 2α, 17α isomer is preferred for biological use.

The reaction scheme involved in the present process is represented below:

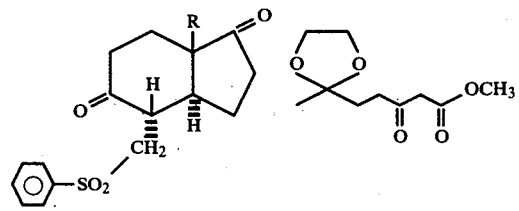

1    2

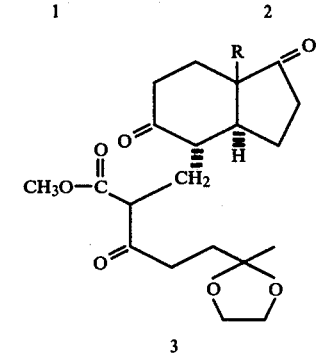

3

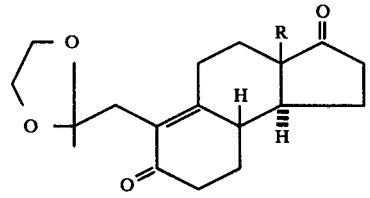

4

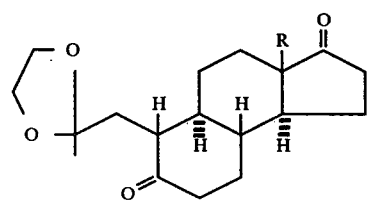

5

-continued

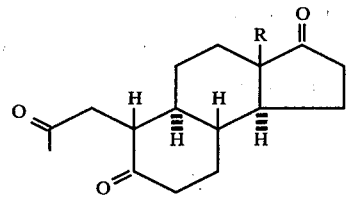

6

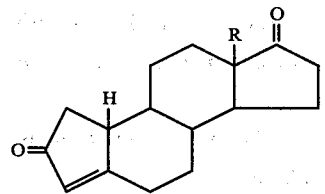

7

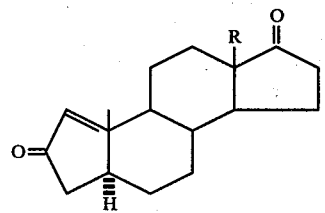

8

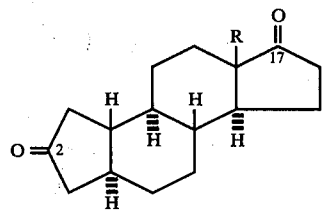

9

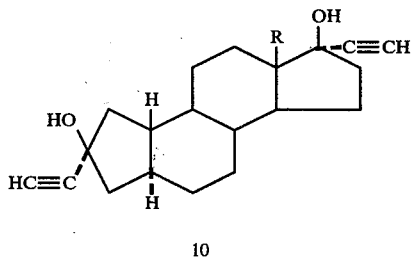

10

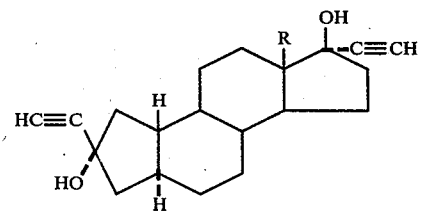

11

-continued

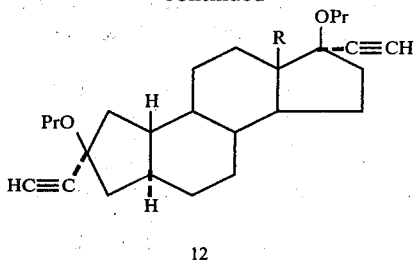

12

The process of the invention involves the use of an approach described by Schering A. G. (see (a) G. Sauer, U. Eder, G. Haffer, G. Neef, and R. Wiechert, *Angew. Chem. Int. Ed. Engl.,* 14, 417 (1975); (b) R. Wiechert, *Angew. Chem. Int. Ed. Engl.,* 16, 506 (1977) and references therein). There is, however, no indication in the Schering disclosures of the possibility of preparing A-nor steroids using this approach.

The starting material for the synthesis of Dinordrin is the known optically active trans-fused bicyclic diketo-sulfone (1) described in the above-mentioned Schering A. G. publications. The crystalline dione (1) is reacted in a non-polar solvent with the anion prepared from 6-(1,3-dioxolan-2-yl)-3-oxoheptanoic acid methyl ester (2), in the presence of sodium or potassium hydride. A triketo-derivative (3) is obtained and this is immediately hydrolized, cyclized and decarboxylated with base, to afford the enone (4) in high yield.

Catalytic hydrogenation of the conjugated ketone (4) gives the dione (5). Acid hydrolysis liberates the cyclo-ethylene ketal, thus providing the crystalline trione (6).

Cyclization of the tricyclic intermediate (6) in methanol solution in the presence of a base gives a mixture of isomeric enones (7) and (8). This mixture can either be separated or immediately submitted to a Birch reduction, followed by oxidation with pyridinium chlorochromate, thus providing the corresponding saturated 2,17-dione (9). This material is shown to be identical by usual criteria (m.p., I.R., N.M.R., etc.) with an authentic sample of the dinor-dione (9), see: P. Crabbé, H. Fillion, Y. Letourneux, E. Diczfalusy, A. R. Aedo, J. W. Goldzieher, A. A. Saikh, and V. D. Castracane, *Steroids,* 33, 85 (1979). This confirms the correct configuration at all asymmetric centres, in particular the A:B trans stereochemistry, i.e. the cyclization process and the Birch reduction of both isomers (7) and (8) are completely stereoselective.

Treatment of the diketo-steroid (9) with an excess of lithium acetylide-ethylenediamine complex under known conditions, furnishes a mixture of 2α- and 2β-isomers, of which the desired 2α-ethynyl steroid (10) may be separated by chromatography. Further esterification of the diol may be performed under known conditions.

The same reaction sequence may be applied to the known optically active 7α-β-ethyl-6H-7,7α-dihydroindane-1,5-dione to give the corresponding 18-homo dinor-steroid.

In addition the same synthetic route may also be applied to the synthesis of A-dinor-steroids (i.e. n in Formula I is 0 so that ring A is a four-member ring) using 5-(1,3-dioxolan-2-yl)-3-oxohexanoic acid methyl ester.

The invention is illustrated by the following example:

EXAMPLE

(a) 5-(1,3-Dioxolan-2-yl)-2-hexanone

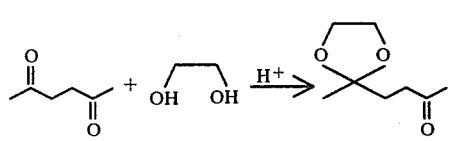

22.8 g (0.2 Mol) Hexanedione-2,5, 12.4 g (0.2 Mol) ethylene glycol, and 0.5 g p-toluenesulphonic acid were refluxed for 18 hours in toluene on a Dean-Stark apparatus. Then the solution was washed twice with $NaHCO_3$-solution, dried over $K_2CO_3$ and concentrated in vacuo. The remaining oil was distilled over a 20 cm-Vigreux column. The middle fractions were redistilled to give the monoketal as a colourless liquid, b.p. 100°–103°/15 mm.

Alternatively the monoketal may also be prepared as follows:

A solution of 2,5-hexadione (23.4 ml, 0.2 mole) and ethyleneglycol (45 ml, 0.8 mol) in toulene (125 ml) was stirred in an ice bath for 15 min. After this time concentrated sulfuric acid (5 ml, 0.09 mole) was added and stirring was continued for 30 min. The lower layer containing mainly ethyleneglycol was separated and extracted with toluene twice. The combined organic layers were washed with a sodium bicarbonate solution (water and NaCl saturated solution). Toluene was evaporated and the remaining viscous liquid containing the starting material contained the mono and di-ketals. These were separated by vacuum distillation, affording the expected monoketal.

NMR (CDCl$_3$): 1.30 (s, 3H); 2.10 (s, 3H); 1.65–2.65 (m, 4H); 3.85 p.p.m. (s, 4H).

IR: 1718 cm$^{-1}$.

(b) 6-(1,3-Dioxolan-2-yl)-3-oxoheptanoic Acid Methyl Ester

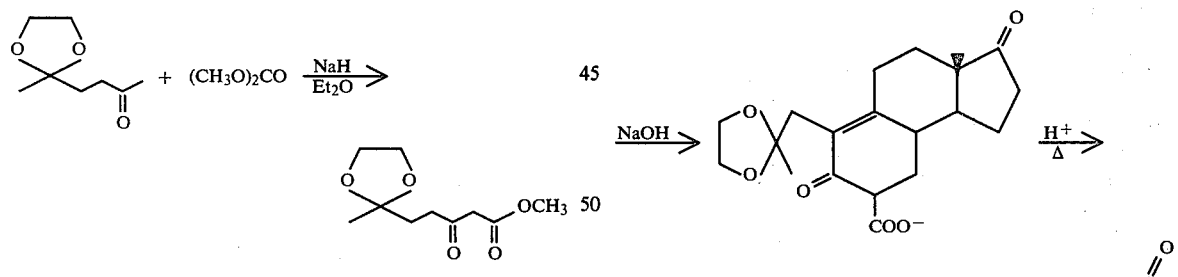

4.32 g Sodium hydride (50% in oil) were washed with pentane, dried and suspended in 30 ml of dry ether. At reflux temperature were added 5.40 g dimethyl carbonate (60 mMol) and then a solution of 4.74 g monoketal (30 mMol) in 20 ml of dry ether. After 4 hours the gas evolution was finished. The mixture was hydrolysed with 5 ml of ethanol, poured on a solution of 7 ml of acetic acid in 100 ml of water, neutralized with NaHCO$_3$ and extracted with ether. The aqueous layer was extracted two more times with ether. The extracts were dried over K$_2$CO$_3$ and evaporated. The residue was distilled in vacuo, to give the ester as an oil.

NMR (CDCl$_3$): 1.30 (s, 3H); 1.60–2.70 (m, 4H); 3.40 (s, 2H); 3.62 (s, 3H); 3.85 p.p.m. (s, 4H).

IR: 1750, 1718 cm$^{-1}$.

(c)

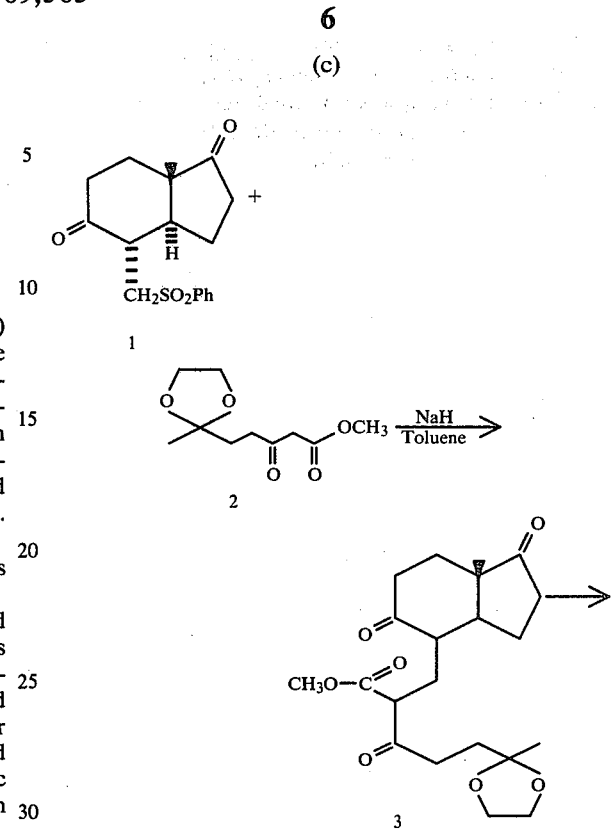

240 mg Sodium hydride (50% in oil, 5 mMol) were suspended in 20 ml of dry toluene. With stirring a solution of 640 mg (2 mMol) of crystalline sulfone (1) (m.p. 92°–94°; [α]$_D$+179°) and 550 mg (2.5 mMol) ketal ester (2) in 20 ml of toluene was added over a period of 15 min. After 2 hours the solvent was removed in vacuo. The alkylation product was not isolated, but hydrolysed, cyclized and decarboxylated to give the unsaturated ketone (4).

The residue was dissolved in 20 ml of methanol and a solution of 0.5 g NaOH in 5 ml of water was added. After 10 hours, methanol was evaporated in vacuo and the aqueous solution was extracted with ether to remove paraffine (from NaH). The aqueous layer was acidified with acetic acid and extracted 3 times with methylene chloride. The extracts were dried over Mg SO₄ and evaporated in vacuo. The residue was refluxed in 30 ml of toluene for 30 min. Then the solvent was removed and the residue purified by chromatography (20 g SiO₂, toluene/ethyl-acetate 4:1), affording the enone (4) as a colourless oil.

(d)

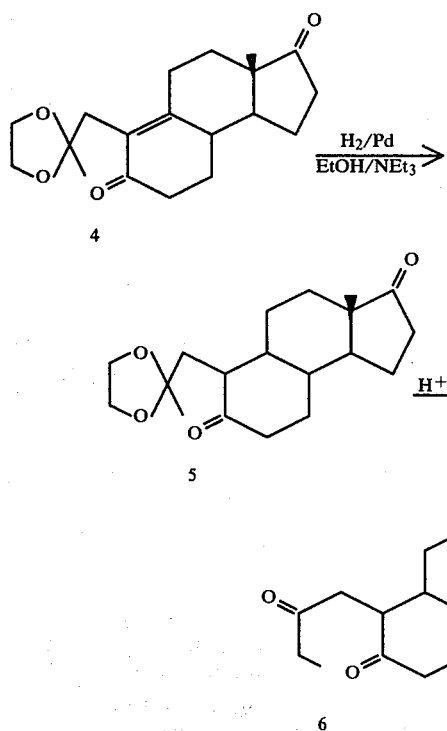

506 mg (1.6 mMol) of Enone (4) were dissolved in 50 ml of ethanol and 0.5 ml of triethylamine. 50 mg of Pd on charcoal (5%) were added and the mixture was stirred at room temperature for 5 hours. The catalyst was filtered off, the solvent evaporated and the residue dissolved in 30 ml of acetone and 2 ml of 1n HCl. After 30 min. the mixture was neutralized with NaHCO₃, acetone was removed in vacuo; the aqueous solution was extracted 4 times with CH₂Cl₂, the extracts dried over MgSO₄ and evaporated. The residue was recrystallized from hexane/ether, providing the triketone (6), m.p. 133°–134°, [α]$_D$+129°;

NMR (CDCl₃): 0.94 (s, 3H); 1.00–3.20, m; 2.20 p.p.m. (s).

IR (Nujol): 1742, 1705 cm⁻¹.

MS (70 eV): 274 (M-2), 258, 233, 220, 219 (100%), 177, 163.

(e)

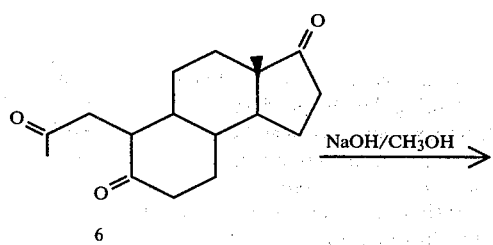

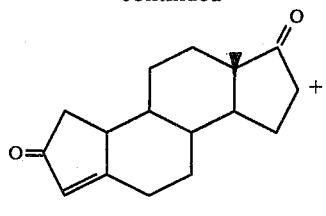

276 mg (1 mMol) Trione (6) were refluxed for 10 hours in a solution of 1.7 g KOH in 30 ml of methanol. After evaporation of the solvent, water was added, acidified with acetic acid, neutralized with NaHCO₃ and extracted three times with CH₂Cl₂. The extracts were dried over K₂CO₃ and the solvent removed in vacuo. The residue crystallized from ether/hexane, to give a crystalline material, m.p. 135°–138°, mixture (1:1) of (7) and (8).

The pure Δ$^{1,10}$-isomer (8) was obtained by recrystallization from hexane: m.p 182°–184°; [α]$_D$+51°; U.V-.$_{max}$229 nm (γ13,000).

NMR (CDCl₃): 0.88 (s, 3H); 0.92 (s, 3H); 0.65–3.00 (m, 18H); 5.67 p.p.m. (s, 1H).

IR (Nujol): 1740, 1702 cm⁻¹.

MS (70 eV): 259 (M+1); 258 (M+, 100%); 240, 214, 202, 187, 174, 173, 160, 159, 149, 146, 145, 134, 132, 131, 119, 117, 108, 107, 106, 105, 97, 96, 95, 94, 93, 91, 81, 79, 77, 67, 66, 65, 55, 53, 51.

(f)

50 mg (0.19 mMol) of the enone isomer mixture in 2 ml of dry ether were added to a solution of 100 mg of lithium in 20 ml of liquid ammonia. After 30 min, 1 g of ammonium chloride was added and the ammonia was allowed to evaporate. The residue was dissolved in water and extracted four times with methylene chloride. The extracts were dried over MgSO₄ and stirred overnight with 0.5 g of Pyridinium chlorochromate. It was hydrolyzed with potassium carbonate solution, separated, washed with 1 n HCl, dried over MgSO₄ and evaporated. The resulting oil was purified by chromatography on 2 g of silica gel (Toluene/ethyl acetate 9:1), to furnish a colourless oil, which crystallized on standing. M.p. (from hexane) 148°-115°. Recrystallization gave the pure sample of (9): m.p. 158°-160°; $[\alpha]_D + 262°$.

IR (Nujol): 1738 cm$^{-1}$ (identical with the spectrum of an authentic sample).

(g)

A current of dry acetylene was passed for 30 minutes through a solution maintained at 0° to 5° C., of 250 mg of the dione 9 of step (f) dissolved in 5 ml anhydrous dimethylsulfoxide (DMSO) to which 272 mg of lithium acetylide-ethylene diamine complex had been added. The reaction mixture was allowed to stand overnight at room temperature after which it was mixed with water. The reaction product comprising about a 3:2 mixture of isomeric 2-ethynyl derivatives was recovered and, after chromatography, the desired 2α, 17α-diethynyl-2β, 17β-dihydroxy-A-nor-5α-estrane (10) was obtained, separated from the 2β-isomer (11). The separation was accomplished by thin layer chromatography using a 7 to 3 cyclohexane-ethyl acetate mixture as a solvent system.

The corresponding diesters, e.g. diacetates, dipropionates, divalerates, dibutyrates, dibenzoates, dienanthates, diundecanoates and the like may be prepared from the diol (10) by conventional esterification techniques. For example, the diol (about 700 mg.) may be dissolved in about 3-5 ml of anhydrous pyridine with the addition of acid anhydride. The reaction mixture is then heated on an oil bath (110°-115° C.) overnight after which methanol is added to remove excess anhydride. The reaction mixture is cooled and the diester extracted, washed and fried, solvent being removed by vacumm. The pure diester isomers may be obtained by chromatography or the diester may be prepared by esterification of the separated hydroxy isomer. For example, esterification with propionic anhydride of the 2β-hydroxyl isomer (m.p. 145°; $[\alpha]_D - 6°$) gives Dinordrin in the optically active form.

The diesters may also be prepared by reacting the diols with the appropriate acid chloride in inert solvent under mild reaction conditions.

Diethers may also be prepared by, for example, reacting the diol with dihydropyran in the presence of an acid such as p-toluene sulfonic acid. Monoethers may also be prepared in conventional fashion.

It is to be noted that, while the foregoing example is concerned with the preparation of 2α, 17α-diethynyl-2β, 17β-dihydroxy-A-nor- 5α-estrane (Dinordrin), the corresponding 18-homo product may be prepared in similar fashion using the known methylene sulfone 7α-β-ethyl-6H-7,7a-dihydroindane-1,5dione as starting material.

The sulfone starting material used in the example was prepared by treatment of optically active (+) 7α-β-methyl-6H-7, 7a -dihydroindane-1,5-dione with paraformaldehyde and benzenesulfinic acid in triethanolamine, and acetic acid, followed by catalytic hydrogenation in the presence of palladium on charcoal. (See again G. Sauer, U. Eder, G. Haffer, G. Neef, and R. Wiechert, *Angew Chem. Intern. Ed.*, 1975, 14, 417). The sulfone was obtained in crystalline form (m.p. 92°-94°; $[\alpha]_D + 179°$). The corresponding ethyl starting material may be obtained in the same way.

It will be recognized that the procedure described above is short, flexible, and easy to perform, thus constituting a useful synthetic approach to the indicated class of biologically important A-nor steroids. It is noteworthy that the cyclization reaction of the intermediates (3), followed by catalytic reduction of the enones (4), condensation and Birch reduction of the cyclopentenones (7) and (8) afforded the dione (9) with the correct stereochemistry at all asymmetric centers, thus showing the total synthetic scheme to be extendible to A-norsteroids with the A:B-trans configuration.

The scope of the invention is defined in the following:
What is claimed is:

1. A process for preparing A-nor and A-nor-18-homo-steroids of the formula:

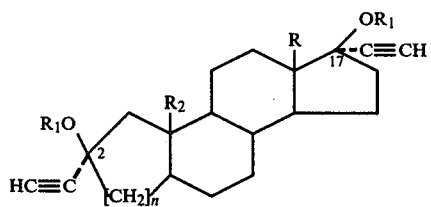

wherein n = 1 or 0, R is methyl or ethyl; R$_1$ is hydrogen or

wherein A is lower alkyl, cyclo-alkyl or aryl; and R$_2$ is hydrogen or methyl which comprises (a) reacting an optically active trans-fused bicyclic diketo-sulfone of the formula:

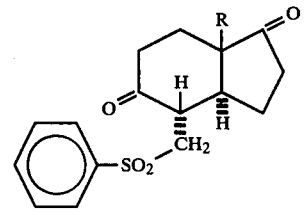

with a 6-(1,3-dioxolan-2-yl)-3-oxoheptanoic acid methyl ester or with a 5-(1,3-dioxolan-2-yl)-3-oxohexanoic acid methyl ester to obtain a triketo derivative;

(b) hydrolyzing, cyclizing and decarboxylating the product of step (a) to obtain an enone;

(c) catalytically hydrogenating said enone to obtain a dione;

(d) acid hydrolyzing to obtain a trione;

(e) cyclizing the product of step (d) to obtain a mixture of isomeric enones;

(f) subjecting said mixture to Birch reduction and oxidation to obtain the corresponding saturated 2,17-dione with the A:B trans stereochemistry;

(g) ethynylating the product of step (f) to obtain a mixture of 2α- and 2β-isomers; and (h) separating the isomers by chromatography.

* * * * *